(12) United States Patent
Knutson et al.

(10) Patent No.: US 8,165,685 B1
(45) Date of Patent: Apr. 24, 2012

(54) SYSTEM AND METHOD FOR THERAPEUTIC NEUROMUSCULAR ELECTRICAL STIMULATION

(75) Inventors: Jayme S. Knutson, Mentor, OH (US); John Chae, Strongsville, OH (US)

(73) Assignee: Case Western Reserve University, Cleveland, OH (US)

( * ) Notice: Subject to any disclaimer, the term of this patent is extended or adjusted under 35 U.S.C. 154(b) by 1061 days.

(21) Appl. No.: 11/536,495

(22) Filed: Sep. 28, 2006

Related U.S. Application Data

(60) Provisional application No. 60/721,771, filed on Sep. 29, 2005.

(51) Int. Cl.
*A61N 1/00* (2006.01)
(52) U.S. Cl. ............................................ 607/48; 607/2
(58) Field of Classification Search ................. 607/2, 48
See application file for complete search history.

(56) References Cited

U.S. PATENT DOCUMENTS

| | | | | |
|---|---|---|---|---|
| 3,083,712 | A | * | 4/1963 | Keegan, Jr. ...................... 607/48 |
| 4,510,939 | A | * | 4/1985 | Brenman et al. .............. 600/384 |
| 4,558,704 | A | * | 12/1985 | Petrofsky ........................ 607/48 |
| 4,697,808 | A | * | 10/1987 | Larson et al. ................... 482/51 |
| 4,785,813 | A | * | 11/1988 | Petrofsky ........................ 607/48 |
| 4,799,487 | A | | 1/1989 | Bleicher |
| 5,540,735 | A | * | 7/1996 | Wingrove ........................ 607/46 |
| 5,562,707 | A | * | 10/1996 | Prochazka et al. ................ 607/2 |
| 6,324,432 | B1 | * | 11/2001 | Rigaux et al. .................... 607/62 |
| 6,516,289 | B2 | * | 2/2003 | David ............................ 600/384 |
| 6,839,594 | B2 | * | 1/2005 | Cohen et al. .................... 607/48 |
| 2002/0161415 | A1 | * | 10/2002 | Cohen et al. .................... 607/48 |
| 2002/0177882 | A1 | * | 11/2002 | DiLorenzo ...................... 607/45 |
| 2003/0139783 | A1 | * | 7/2003 | Kilgore et al. .................. 607/49 |
| 2004/0147975 | A1 | * | 7/2004 | Popovic et al. ................. 607/48 |
| 2004/0267331 | A1 | * | 12/2004 | Koeneman et al. ............. 607/49 |

FOREIGN PATENT DOCUMENTS

| EP | 506398 A1 | * | 9/1992 |
|---|---|---|---|
| GB | 2227173 A | * | 7/1990 |

* cited by examiner

*Primary Examiner* — Nicole F Lavert
(74) *Attorney, Agent, or Firm* — Kraguljac Law Group LLC

(57) ABSTRACT

A system for neuromuscular electrical stimulation therapy includes one or more sensors for sensing the position or the muscle contractions of a body part, such as an arm, hand, finger, leg, etc.; a stimulator in communication with the sensor or sensors; and two or more electrodes that can be positioned to activate the paralyzed body part. Based on signals from the one or more sensors, the stimulator can regulate the stimulation provided through the electrodes, including the intensity and duration of the electrical stimulation signal. The sensors can be assembled in a wearable article, such as a glove, sock, or sleeve, to monitor the position or muscle contractions of the healthy body part. The electrodes also may be assembled in a wearable device that allows customized placement of those electrodes.

8 Claims, 4 Drawing Sheets

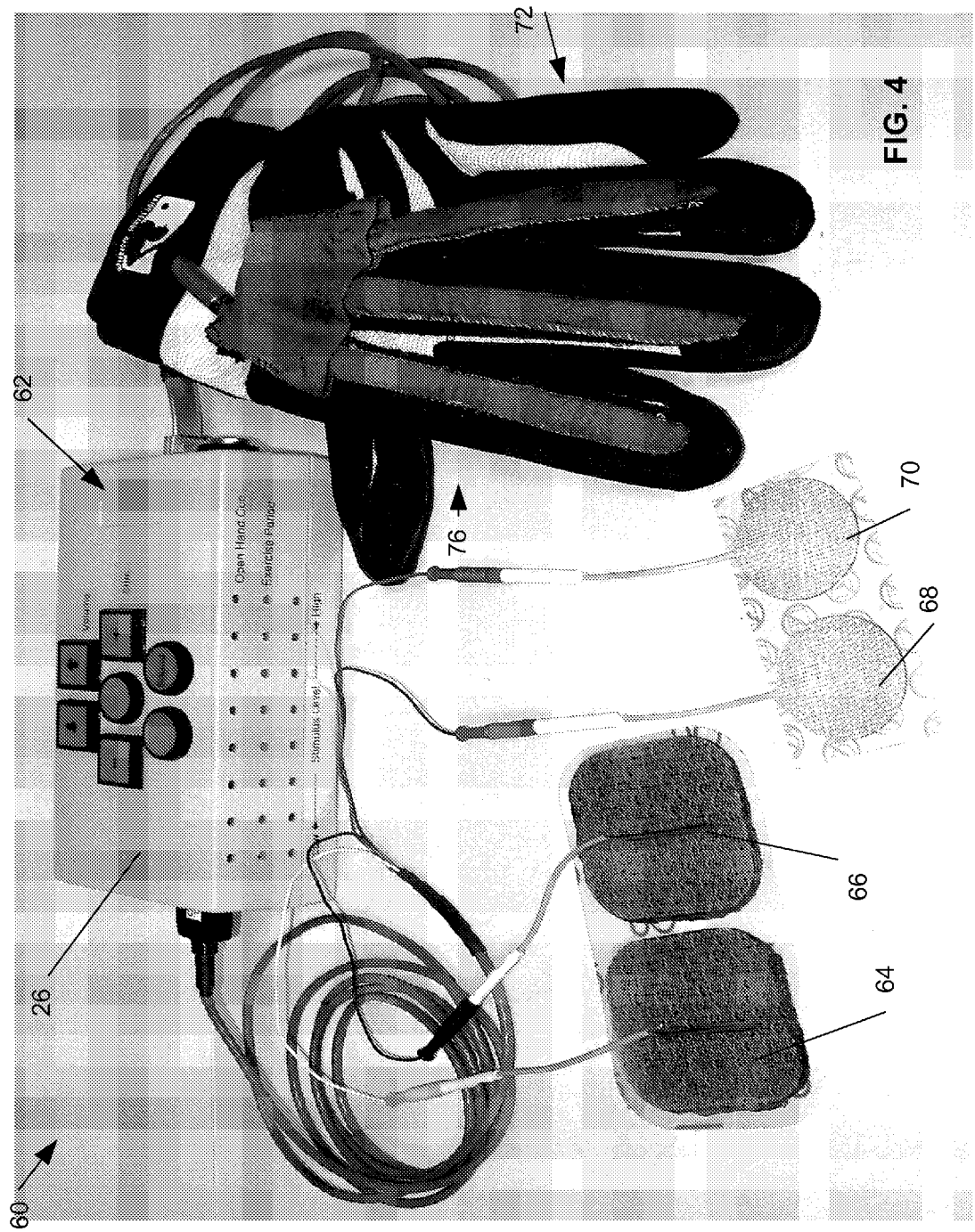

SYSTEM AND METHOD FOR THERAPEUTIC NEUROMUSCULAR ELECTRICAL STIMULATION

This invention claims the benefit of U.S. Provisional Patent Application No. 60/721,771, filed on Sep. 29, 2005, which is hereby incorporated herein in its entirety.

FIELD OF THE INVENTION

This invention relates generally to a therapeutic treatment for paralysis on one side of a body, and in particular to a system and method for neuromuscular electrical stimulation therapy.

BACKGROUND

Paralysis on one side of the body can result from stroke, traumatic brain injury, spinal cord injury, or disease. Depending on the nature of the neural damage, it is possible for paralysis patients to recover some degree of motor control. Numerous techniques have been used to facilitate a patient's motor recovery. These include constraint-induced movement therapy, robot-assisted movement, and several methods using neuromuscular electrical stimulation (NMES) of paralyzed muscles.

These techniques also include devices and methods that use permanently implanted electrodes to overcome paralysis. One such device is shown in U.S. Pat. No. 4,799,487, which discloses a device for the re-animation of a paralyzed face. The device includes electrodes implanted in muscles on a healthy side of a face for sensing contractions and sending signals to a processor, which in turn processes these signals and re-transmits them to other electrodes implanted in the counterpart muscles in a paralyzed side of the face to stimulate the counterpart muscles to contract.

SUMMARY

More effective rehabilitation techniques are desired to facilitate recovery of motor control after paralysis. Many of the current therapies require some residual movement of the paralyzed part of the body and therefore are not applicable to severely disabled patients. In addition, some of the current techniques require significant amounts of therapist time, intensive therapy sessions or expensive equipment, which make these therapies challenging to implement in the present health care environment. Furthermore, permanently implanted devices, such as in the patent described above, have the added costs of surgery, carry risks of complications, and may require continuous operation in order to maintain the desired effect.

A system provided by the present invention includes one or more sensors for sensing the position or the muscle contractions of a body part, such as an arm, hand, finger, leg, etc., a stimulator in communication with the sensor or sensors and two or more electrodes that can be positioned to activate the corresponding paralyzed body part. Based on signals from the one or more sensors, the stimulator regulates the degree of stimulation provided through the electrodes, and in the process uses the patient's motor intention to move the paralyzed body part. The sensors can be assembled in a wearable article, such as a glove, sock, or sleeve, to monitor the position or the muscle contractions of the healthy body part. The electrodes also may be embedded in a wearable device.

The stimulator includes a pulse generator, a processor, such as a microprocessor, and related electronic elements, such as a memory, input and output devices, and communication devices, for example, for communicating with the sensors and the electrodes and controlling the stimulus delivered by the electrodes. The stimulator can control both the stimulation intensity and the relative timing of stimulation delivery to each electrode. The stimulation intensity is modulated in proportion to the position of the healthy body part or the magnitude of muscle contraction of the healthy body part, as detected by the sensors. In this way, the patient gains the ability to modulate control of the impaired body part via control of the healthy body part. The stimulator can also output audio and light cues to prompt the patient to move the healthy body part and thereby perform a prescribed exercise. It is believed that over time these exercises will help the patient regain control of the impaired body part, either as new neural pathways are formed or as the patient's body repairs damage that caused the paralysis.

In particular, the present invention provides a system for therapeutic neuromuscular electrical stimulation that includes means for sensing the position or the muscle contractions of a first body part and providing an output representative thereof, and means for stimulating a second body part based on the position of the first body part or the magnitude of muscle contraction of the first body part. The sensing means can include a sensor, and the stimulating means can include a stimulator and a pair of electrodes.

The present invention also provides a system that includes a glove having a plurality of sensors that sense the position of several fingers of a first hand, a plurality of electrodes positioned to stimulate muscles that control an opposite second hand, and a stimulator in communication with the sensors and the electrodes that causes the electrodes to stimulate the muscles that control the second hand based on information from the sensors about the position of the fingers of the first hand. The stimulator includes an output device that can be used to cue the patient to move the first hand to control movement of the second hand.

An exemplary method for therapeutic neuromuscular stimulation comprises the steps of correlating the position of a first hand or the magnitude of the muscle contractions of a first hand with a degree of electrical stimulation provided to a second hand, detecting the position or the muscle contraction of the first hand, and electrically stimulating muscles of the second hand to a degree based on the position of the first hand or the magnitude of muscle contraction of the first hand. Another exemplary method for therapeutic neuromuscular stimulation comprises the steps of detecting the position or the muscle contraction of a first body part, and electrically stimulating muscles of a second body part at an intensity corresponding to the position of the first body part or the magnitude of muscle contraction of the first body part. The method can further include the step of signaling a patient to move the first body part to control movement of the second body part.

BRIEF DESCRIPTION OF THE DRAWINGS

FIG. 4 is a perspective view of an exemplary embodiment of the system shown schematically in FIG. 3.

DETAILED DESCRIPTION

The present invention provides a system and method for therapeutic neuromuscular electrical stimulation, in other words a therapy with electrical stimulation of paralyzed muscles, where the initiation, duration, and intensity of electrical stimulation and the consequent movement of the paralyzed body part is controlled by the patient. Although the paralysis is evidence of an impaired ability to intentionally or consciously control the paralyzed muscles, movement of the body part opposite the one being stimulated can be used as a proxy for cognitive intent. In other words, a healthy arm, leg, hand, foot, finger, thumb, or other controllable body part is used to cause movement of a paralyzed arm, leg, hand, foot, finger, thumb, etc., or portion thereof. The position of the healthy body part or the magnitude of muscle contraction in the healthy body part is translated into a proportional intensity electrical stimulation delivered to the paralyzed muscles. In this way, the patient can control the degree of stimulation of the paralyzed muscles, and therefore the degree of movement of the paralyzed body part, through graded movement in the healthy body part.

Figure 1:
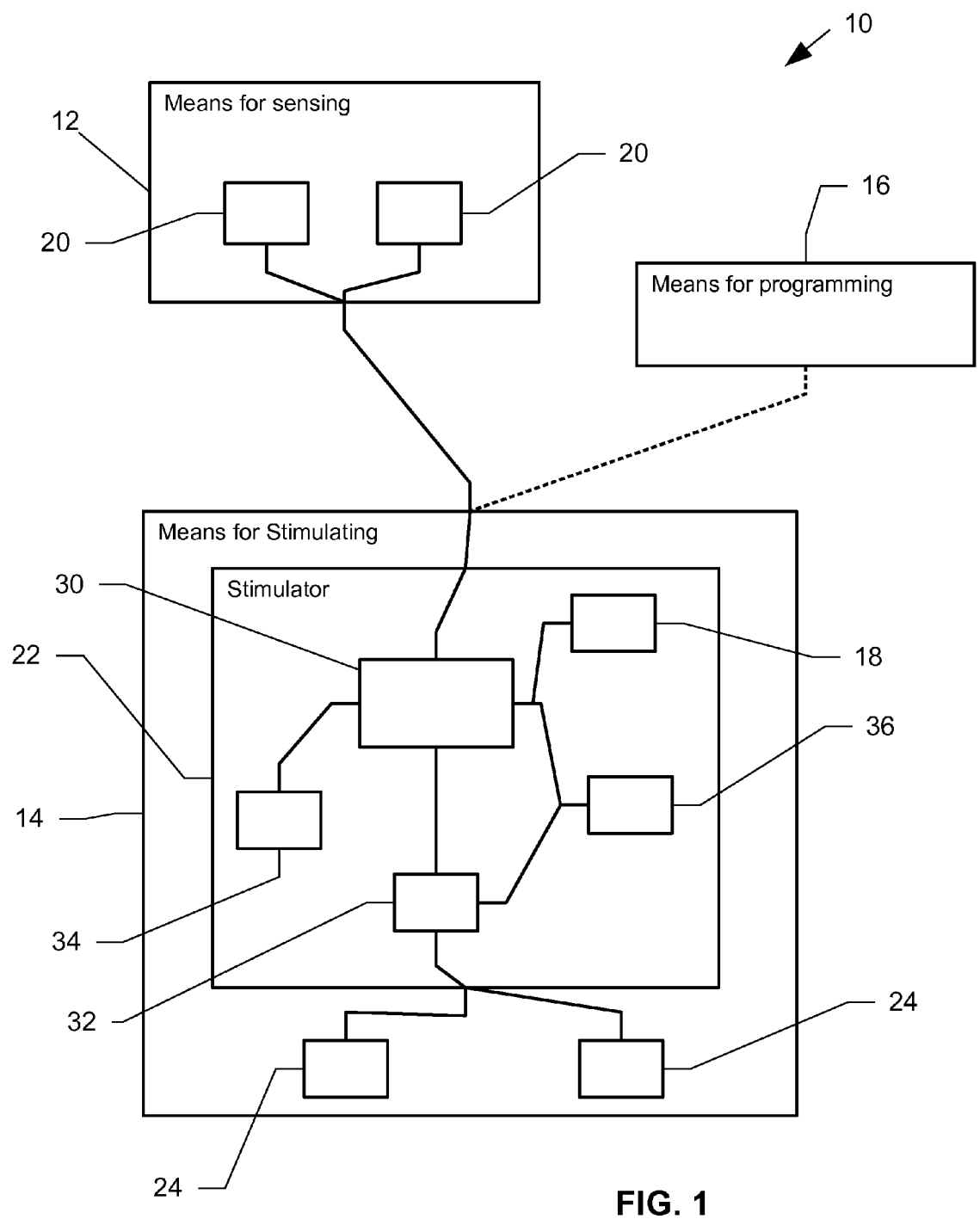
FIG. 1 is a generic schematic of a system provided by the invention.

Referring now to the drawings in detail, and initially to FIG. 1, the present invention provides an exemplary therapeutic system 10 with neuromuscular electrical stimulation that includes means for sensing 12 the position or muscle contraction in a healthy first body part, and means for stimulating 14 paralyzed muscle to control an impaired second body part in proportion to input from the sensing means 12. The system 10 can also include means for programming 16 the stimulating means 14 with customized stimulus intensities and patterns for a particular patient. A therapeutic method includes using this electrical stimulation system 10 to perform symmetric bilateral active repetitive movement exercises, which typically can be self-administered by the patient, and to practice functional tasks using the paralyzed body part. For exercise therapy, the stimulating means 14 also generally includes means for signaling 18 the patient to move the healthy body part or to relax the healthy body part in a predetermined cycle.

The means for sensing 12 the position or muscle contraction of the healthy body part typically includes at least one sensor 20, and generally more than one sensor. The sensors 20 detect the position or muscle contractions of an unimpaired or healthy body part. The sensors generally can be separated into two main categories. The first category includes position sensors, which sense the instantaneous position of the unimpaired body part. These sensors can be variable resistive in nature (e.g. bend sensors, potentiometers), electromagnetic (e.g. Hall effect sensor, accelerometer), fiber optic, or any other type of sensor that can detect instantaneous position of a body part with adequate resolution. The second category of sensors includes electromyographic (EMG) sensors, which sense the electrical activity in muscles of the unimpaired body part as they contract and relax. These sensors are actually electrodes and may be surface electrodes that adhere to the skin over the muscle of interest or may be percutaneous electrodes, which are fine wires inserted into the muscle and remain in place for the duration of the treatment regimen. The sensors 20 used in the therapeutic system 10 can include combinations of different types of sensors and sensors from either, both, or neither category. In an alternative category, nerve sensors could be used to detect nerve activity, but probably would not provide a significantly more useful input to the stimulating means 14.

Finally, the sensor or sensors 20 can be assembled in a wearable article, such as a sock, glove, sleeve, cuff, etc., to facilitate placement of the sensor or sensors on the healthy body part. The stimulating means 14 typically supplies the power for each sensor 20, but it is conceivable that the sensors could have their own common power supply, or individual power supplies could be provided for each sensor.

The stimulating means 14 includes a stimulator 22, and two or more electrodes 24. The stimulator 22 may be provided within a portable housing 26 (FIG. 4), and means for communicating (not specifically shown) also may be at least partially enclosed in the housing. The means for communicating connects the stimulator 22 to the electrodes 24 and the sensing means 12 and may be at least partially incorporated in one or more elements of the stimulator 22.

Communication between the sensing means 12 or the electrodes 24 and the stimulator may be either hardwired (as in FIGS. 3 and 4) or wireless, although communications between the sensing means 12 the stimulator 22 are more likely to be wireless than communications between the stimulator 22 and the electrodes 24.

The stimulator 22 also may be referred to as a controller, and typically includes a processor 30, such as a microprocessor; an electrical pulse generator 32; a memory 34; and a power supply 36. The processor 30 interprets inputs from the sensing means 12 that are used to calculate stimulus parameters. Under the direction of the processor 30, the pulse generator 32 outputs a balanced biphasic electrical current waveform with the pulse amplitude, frequency, and duration calculated by the processor 30. A separate stimulus channel may be provided for sending an electrical stimulation signal to each electrode 24. The pulse generator can include a multichannel electrical pulse generator with an output for each stimulus channel. The memory 34 can store data provided from the sensing means 12 and record information representing the usage times and durations, as well as the pulses generated by the pulse generator 32. The memory 34, or memory integral with the processor 30, stores software installed by the programming means 16 for carrying out a therapy regimen. The power supply 36, such as a rechargeable battery or a connection to an electrical outlet, supplies power to the system 10.

The stimulator 22 also includes one or more inputs, including connections to the sensing means 12 and the programming means 16. If the stimulator 22 has a rechargeable battery, the stimulator also can be connected to a battery charger to recharge its battery.

The stimulator 22 also can include one or more outputs, including connections to the signaling means 18, which includes output devices for providing cues to the patient, such as a display, a light, or a speaker, for example; output channels for the electrical stimulation signals; connections for the programming means 16; etc. The outputs can provide the patient or other operator with audible or visual feedback of the operation of the stimulator 22, including stimulus intensity and the state of the stimulator and its battery, for example.

The electrodes 24 are connected to the stimulator 22 via the pulse generator 32 for delivering neuromuscular stimulation to the paralyzed body part. The electrodes 24 typically include at least one positive anode and one or more stimulating electrodes. The stimulating electrodes can be surface-type electrodes that are reusable or disposable, or may be embedded in a wearable article or attached singly or in a group using a temporary adhesive. Alternatively, the electrodes can be temporarily inserted through the skin into muscle, as with acupuncture needles, for a therapy session. The electrodes also may be implanted for the duration of a treatment regimen.

Placement of the electrodes 24 typically is customized for optimum functional stimulation for each individual patient. For patients to perform exercise therapy on their own, such as at home, after customized placement, they can reapply the electrodes to the paralyzed body part. To assist the patients or their caregivers in properly positioning surface electrodes, for example, for each exercise session, the outline of the electrodes can be traced on the skin with a pen or other marking means after customized placement. Also, pictures showing the placement of the electrodes can be taken to facilitate replacement of the electrodes in approximately the same position. Since surface electrodes are not extremely precise in their application of a stimulation signal, this is generally sufficient. The electrodes also can be color-coded or otherwise marked to help differentiate the electrodes and ensure that the correct electrode is attached to the expected channel of the stimulator 22.

The electrodes 24 typically are driven by a signal from the pulse generator 32 in the stimulator 22. The electrodes 24 conceivably could be powered by a common or individual power supplies controlled by the stimulator 22. In this scenario, the stimulator can provide a signal that initiates application of a stimulus that is driven or amplified by the electrode power supply at a programmed intensity, duration, pattern or combination thereof.

The programming means 16 is connected to the stimulating means 14 in general, and the stimulator 22 more particularly, only temporarily, such as during set-up and calibration. The programming means 16 can include a personal computer, such as a laptop computer, a hand-held personal computer, a desktop computer, a logic device, etc. The programming means includes software for programming the stimulator's processor to calculate stimulation intensities for each stimulus channel that are proportional to the sensor input. In addition, the programming means may include software for programming the stimulator to output light and sound cues that assist the patient or other operator in using the system, as noted above. The means for programming 16 also can be used for retrieving logged usage data from the memory 34 of the stimulator 22. The software in the means for programming 16 also may be used to calibrate the system 10 for a particular patient.

Calibrating the system 10 for a particular patient upon initial set-up can include correlating body part position or magnitude of muscle contraction with a degree of electrical stimulus. Calibration can include determining thresholds and maximum stimulus intensities for each stimulus channel; determining minimum and maximum input signals from the sensors 20; and determining optimum electrode locations on or in muscles for effective stimulation. The minimum stimulus intensity can be defined as the pulse duration associated with the first perceived sensation or muscle twitch. The maximum stimulus intensity can be defined as the pulse duration or amplitude that produces maximum movement in the impaired body part without discomfort. In addition, the input signal from the healthy first body part can be calibrated to modulate the stimulation from minimum to maximum as the first body part is moved through a range of motion from a resting posture to a maximum volitional posture removed from the resting posture.

Figure 2:
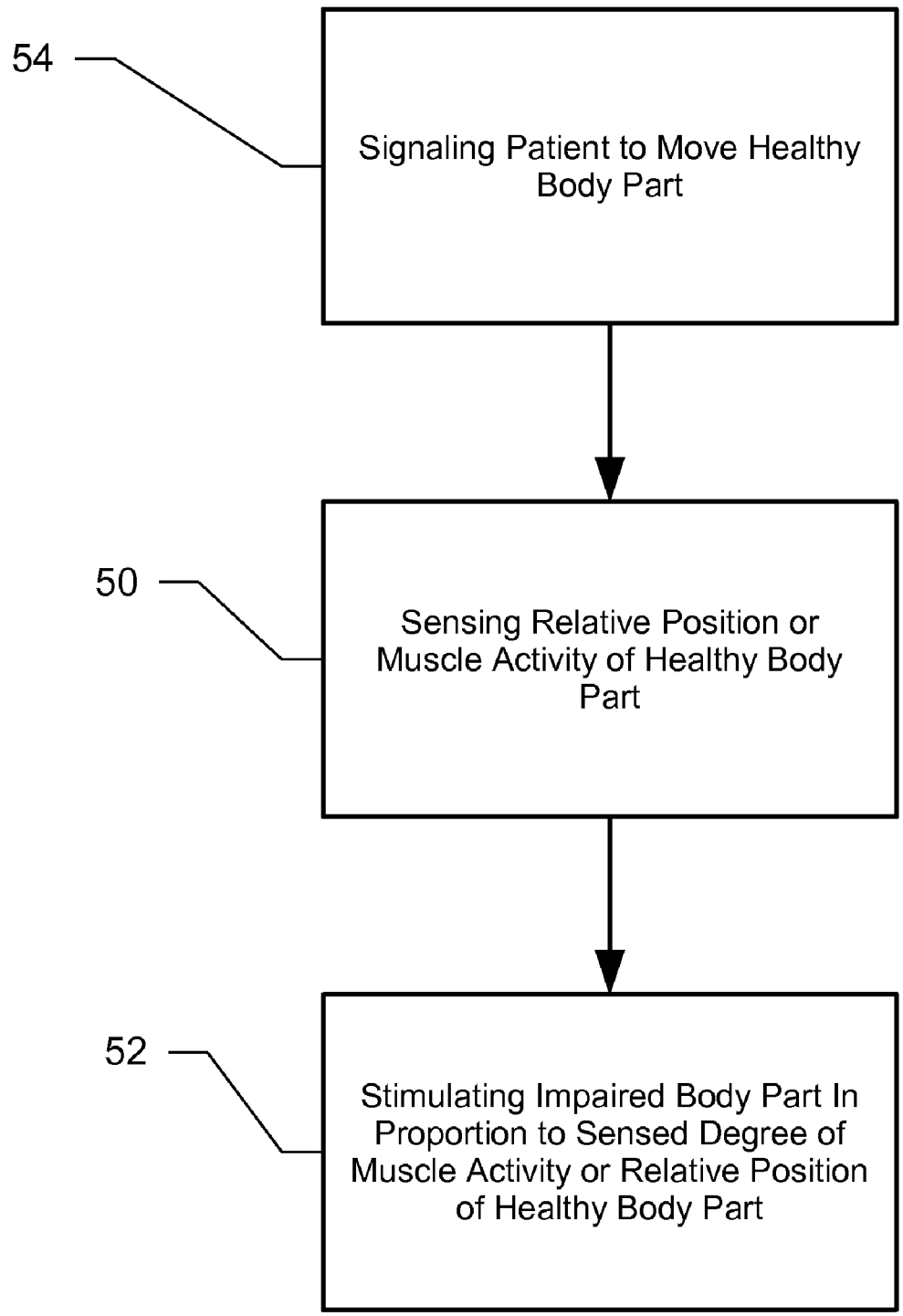
FIG. 2 is a flowchart illustrating a method of treatment provided by the present invention.

Referring briefly to FIG. 2, an exemplary therapeutic method using neuromuscular electrical stimulation includes the steps of sensing position or muscle contraction of a healthy first body part (at 50), and electrically stimulating an impaired second body part based on the position of the healthy first body part or magnitude of muscle contraction in the healthy first body part (at 52). For exercise therapy, the method also includes the step of signaling the patient to move the healthy body part to control the impaired body part (at 54). For example, light or sound cues prompt the patient to perform simultaneous bilateral (both body parts) active, repetitive movement exercises. This activity is believed to increase the effectiveness of electrical pathways from the patient's brain to the muscles in the impaired body part and thereby restore function to the impaired body part. The system 10 (FIG. 1) also may be used in functional therapy sessions, including physical and occupational therapy, where the patient is encouraged to use the system to perform functional tasks using the impaired body part.

While the neurophysiological basis for motor recovery is not completely understood, sensory input, experience, and learning can improve motor function. Moreover, neuroplasticity is facilitated by goal-oriented active, repetitive movement training. Rehabilitation therapies that generate synchronous activation of neurons along motor and sensory pathways might facilitate synaptic remodeling along those neural paths, possibly leading to neural reorganization and improved motor recovery.

This treatment method incorporates several rehabilitation techniques associated with motor recovery. Repetitive motion is incorporated by having the patient perform daily exercises consisting of repetitive movement in response to cues. This movement is active, not passive, because the stimulated movement is produced only in response to movement of the unimpaired or healthy body part. Task-specific or goal-oriented motion is incorporated through therapist-supervised sessions, where patients are coached to use their impaired body part in functional tasks graded by difficulty. Bilateral symmetric movement of the impaired and nonimpaired body parts is implicit in the system as participants are instructed to volitionally assist the stimulation with their impaired body part to provide volitional neural activity in the brain. Creating the perception of restored motor control in the impaired body part is incorporated by coupling motor intention to motor response and proprioceptive (the perception of body position) and cutaneous (touch sensation) feedback, potentially giving the participant the perception that he or she has regained control over their impaired body part. Over time, this perception is believed to contribute to making recovery more likely.

Figure 3:
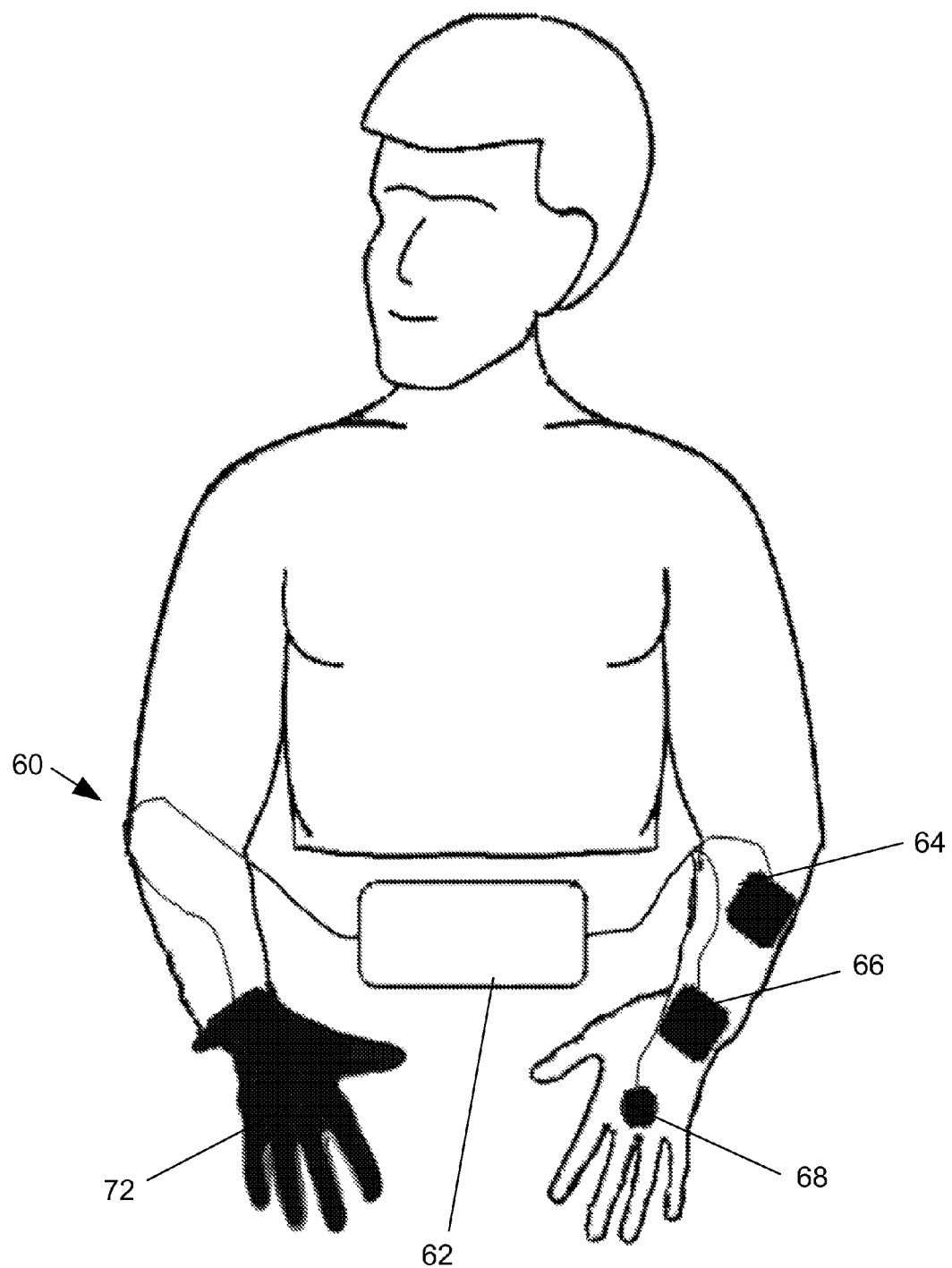
FIG. 3 is a schematic view of an exemplary system provided by the invention.

A specific example of a system 60 and method for therapeutic neuromuscular electrical stimulation will be described with reference to FIGS. 3 and 4. Unless otherwise specified, the elements of this system 60 are equivalent to corresponding elements of the system 10 described with reference to FIG. 1. A patient who has survived a stroke may have some degree of paralysis on one side of the body only. One of the more common problems for stroke survivors is difficulty in opening their hand on the impaired side of their body. The exemplary system 60 shown in FIGS. 3 and 4 has been used to help patients exercise their control over the opening of the impaired hand. The muscles that open the impaired hand are stimulated, via a stimulator 62 and electrodes 64, 66, 68, and 70 placed on the patient's impaired arm or hand. When the stroke survivor opens their opposite, unaffected or healthy hand, the hand position is detected by the sensors (not shown) and communicated to the stimulator 62. Stimulating those muscles causes the patient's impaired hand to open. By intentionally opening the unaffected hand, the patient signals the stimulator 62 to deliver a proportional intensity stimulation to the extension muscles of the paralysized thumb and one or more fingers via the electrodes 64, 66, 68 and 70.

In this system a plurality of sensors (not shown) are assembled in a glove 72 for the patient's healthy hand. Specifically, the glove 72 has a sensor assembly 76 attached to the back side of the hand, which can be removed and attached to different size gloves as needed. The sensor assembly 76 consists of three bend sensors enclosed in cloth sheathes that attach with hook-and-loop fasteners to the glove over the index, middle and ring fingers. When the fingers open and close proportional impendence changes in the sensors modulate the analog voltage input to the stimulator 62. The stimulator 62 delivers up to three independent monopolar channels of biphasic current to the electrodes 64, 66, 68, and 70 and modulates the stimulation intensity from each channel in response to an analog input from the sensors in the glove 72. Self-adhering pre-gelled electrodes connected to the stimulator are used to activate extrinsic and intrinsic finger and thumb extensors in the impaired arm.

Setting up and calibrating the system 60 for a particular patient can include determining the electrode positions and stimulation intensities that produce functional hand opening. For example, an electrode 66 can be placed over the dorsum of the wrist as an anode. To produce finger extension, the extensor digitorum communis (EDC) is targeted with an electrode 64 placed on the dorsal mid-forearm. If the forearm electrode 64 did not also produce thumb extension, another electrode can be placed either distal to the EDC electrode to recruit the extensor pollicis longus (EPL) or at the base of the thumb to recruit the abductor pollicis brevis (AbPB). If extension of the proximal interphalangeal joints of the fingers is incomplete with EDC stimulation, another electrode 68 can be placed on the dorsum of the hand to activate the dorsal interosseous (DI) muscles. Finally, the extensor indicis proprius (EIP) in the forearm can also be targeted to enhance extension of the index finger.

Calibrating the system 60 can also include determining the minimum and maximum stimulus intensities for each stimulating electrode 64, 68, and 70. The minimum intensity can be defined as the pulse duration associated with the first perceived sensation or muscle twitch. The maximum intensity can be defined as the pulse duration that produces maximum finger or thumb opening without discomfort. In addition, the input signal from the glove 72 can be calibrated to modulate the stimulation of each channel from minimum to maximum as the gloved hand is moved from a closed resting posture to a fully open posture, since these postures can differ between patients.

The sound and light cues for hand opening also can be programmed during set-up to turn on and off with a duty cycle comfortable for the particular patient. For example, this can be twelve seconds on, twenty-four seconds off for one patient and eight seconds on, eight seconds off for another patient.

Unlike other electrical stimulation systems and methods, the system provided by the invention maximizes the degree of coupling between motor intention (the central or pre-synaptic activity in the patient's brain telling a body part to move) and stimulated motor response (peripheral, post-synaptic activity of muscles causing a body part to move) by making the stimulation intensity proportional to the amplitude of the control signal (the degree to which the healthy hand is opened). With this scheme, the stroke survivor not only controls the onset of the stimulation, but also the duration and intensity of stimulation and the resultant degree of hand opening.

An exemplary therapy regimen includes using the system for exercise and functional activity. To exercise, the stroke survivor uses the stimulation system to repeatedly open their paralysized hand in response to audible or visual cues output from the stimulator. The sound and light cues from the stimulator prompt the patient when to attempt to open and when to rest their hands according to a pre-programmed duty cycle. In occupational or functional therapy sessions, the stroke survivor can use the system to practice performing tasks with the paralysized hand. The purpose of the therapy is to accelerate and improve motor recovery and prevent severe chronic disability and generally to improve hand function; this system is not intended to be a permanent means for a patient to control the impaired hand, such as in a prosthesis.

During an initial trial, patients were asked to use this system to perform two one-hour sessions of active, repetitive hand opening exercises every day. An exemplary exercise session consisted of three 15-minute sets separated by five minutes of rest. During a set, light and sound cues from the stimulator prompted the patient to open and then relax both hands at the duty cycle programmed for them. At functional therapy sessions, the patients practiced a finger movement control task for fifteen minutes, followed by practice using the impaired hand to perform several functional tasks for approximately seventy-five minutes. These tasks were designed to require the patient to concentrate on controlling the degree of hand opening, to develop motor skill, and to provide a strong perception that their motor intention was producing the desired modulated motor output. In other words, to show the patients how they could control the degree of movement of their impaired hand. Functional task practice can include, for example, repeatedly squeezing and releasing a foam ball, stacking blocks with controlled release, picking up and releasing cups of various diameters without over turning them, drinking or pouring from a cup, and using scissors. The more difficult tasks require the ability to slowly or carefully open the hand and coordinate hand function with movement of the arm.

The results of the initial trial were positive. The patients quickly and easily learned to operate the system and to apply the electrodes correctly. And these preliminary initial results suggest a positive effect on motor impairment from such contralaterally-controlled neuromuscular electrical stimulation therapy.

What is claimed is:

1. A method for therapeutic contralaterally controlled functional electrical stimulation, comprising:
   sensing an intentional muscle contraction of a first body part through one or more sensors associated with a wearable article;
   correlating the intentional muscle contraction of the first body part with a degree of electrical stimulation to be provided to a second homologous contralateral body part to the first body part; and
   electrically stimulating the second body part at an intensity directly controlled by and solely a function of the sensed intentional muscle contraction of the first body part.

2. A method for therapeutic contralaterally controlled functional electrical stimulation, comprising:
   detecting a magnitude of an intentional muscle contraction of a muscle associated with a first body part through one or more sensors associated with a wearable article, where the muscle was intentionally contracted by performing a movement of the first body part; and
   electrically stimulating a second body part that is homologous and contralateral to the first body part, at an intensity corresponding to and solely determined by the magnitude of the intentional muscle contraction of the muscle associated with the first body part.

3. The method of claim 2, comprising signaling a patient to move the first body part to control stimulated movement of the second body part.

4. The method of claim 2, where the first body part is a functional body part that can be intentionally controlled and where the second body part is an at least partially dysfunctional body part.

5. The method of claim 2, comprising:
   establishing a minimum electric current intensity associated with muscle stimulation associated with the first body part being at rest; and
   establishing a maximum electrical current intensity associated with muscle stimulation associated with the second body part being at a maximum comfortable muscle stimulation removed from an unstimulated muscle state.

6. The method of claim 1, comprising signaling a patient to move the first body part to control stimulated movement of the second body part.

7. The method of claim 1, where the first body part is a functional body part that can be intentionally controlled and where the second body part is an at least partially dysfunctional body part.

8. The method of claim 1, comprising:
receiving an electrical signal from the one or more sensors associated with the wearable article worn by the first body part; and
sensing the intentional movement of the first body part as a function of the electrical signal.

\* \* \* \* \*